(12) United States Patent
Chodkowski (10) Patent No.: US 11,065,411 B2
(45) Date of Patent: Jul. 20, 2021

(54) CUSTOMIZED SEALING MEMBER FROM BLANK

(71) Applicant: KONINKLIJKE PHILIPS N.V., Eindhoven (NL)

(72) Inventor: Lauren Patricia Chodkowski, Pittsburgh, PA (US)

(73) Assignee: Koninklijke Philips N.V., Eindhoven (NL)

( * ) Notice: Subject to any disclaimer, the term of this patent is extended or adjusted under 35 U.S.C. 154(b) by 284 days.

(21) Appl. No.: 16/064,687

(22) PCT Filed: Dec. 12, 2016

(86) PCT No.: PCT/IB2016/057521
§ 371 (c)(1),
(2) Date: Jun. 21, 2018

(87) PCT Pub. No.: WO2017/109630
PCT Pub. Date: Jun. 29, 2017

(65) Prior Publication Data
US 2018/0369530 A1    Dec. 27, 2018

Related U.S. Application Data

(60) Provisional application No. 62/270,820, filed on Dec. 22, 2015.

(51) Int. Cl.
*A61M 16/06*     (2006.01)
*A61B 5/00*      (2006.01)
(Continued)

(52) U.S. Cl.
CPC ....... *A61M 16/0605* (2014.02); *A61B 5/0064* (2013.01); *A61B 5/1077* (2013.01);
(Continued)

(58) Field of Classification Search
CPC ........... A61M 16/06–0655; A61M 2016/0661; A61M 2207/00–10; A61B 5/0062–0066;
(Continued)

(56) References Cited

U.S. PATENT DOCUMENTS

| 6,728,589 B1 | 4/2004 | Delache |
| 2004/0079374 A1 | 4/2004 | Thornton |

(Continued)

FOREIGN PATENT DOCUMENTS

| WO | WO2007145534 A1 | 12/2007 |
| WO | WO2008042705 A2 | 4/2008 |

(Continued)

*Primary Examiner* — Kendra D Carter
*Assistant Examiner* — Elliot S Ruddie
(74) *Attorney, Agent, or Firm* — Michael W. Haas (57) ABSTRACT

A customized sealing member is for a customized mask of a pressure support system. The steps to manufacture the customized sealing member include generating surface geometry data of a face of a patient, the surface geometry data corresponding to and representing a surface geometry of the face of the patient; generating customization data using the surface geometry data, the customization data representing how a seal blank should be modified for the patient; and customizing the seal blank using the customization data such that the customized seal blank is shaped according to the customization data.

5 Claims, 5 Drawing Sheets

(51) Int. Cl.
  *A61B 5/107* (2006.01)
  *B33Y 80/00* (2015.01)
(52) U.S. Cl.
  CPC ..... *A61M 16/06* (2013.01); *A61M 2016/0661* (2013.01); *A61M 2207/00* (2013.01); *B33Y 80/00* (2014.12)
(58) Field of Classification Search
  CPC ........ A61B 5/1077–1079; B33Y 80/00; A62B 23/025; A41D 13/11
  See application file for complete search history.

(56) References Cited

U.S. PATENT DOCUMENTS

| | | | | |
|---|---|---|---|---|
| 2008/0078396 | A1* | 4/2008 | Janbakhsh | A61M 16/06 128/205.25 |
| 2012/0305003 | A1 | 12/2012 | Mark | |
| 2014/0352134 | A1* | 12/2014 | Ho | A61M 16/06 29/592 |
| 2015/0151066 | A1* | 6/2015 | Chodkowski | A61M 16/06 128/206.24 |
| 2015/0157822 | A1* | 6/2015 | Karpas | B29C 33/52 128/206.24 |
| 2015/0273170 | A1* | 10/2015 | Bachelder | A61M 16/0605 128/205.25 |
| 2015/0314096 | A1* | 11/2015 | Chodkowski | A61M 16/06 128/206.24 |

FOREIGN PATENT DOCUMENTS

| | | | |
|---|---|---|---|
| WO | WO2011049548 | A1 | 4/2011 |
| WO | WO2013068950 | A1 | 5/2013 |
| WO | WO2014091370 | A1 | 6/2014 |
| WO | WO2014155270 | A1 | 10/2014 |
| WO | WO-2015195303 | A1 * | 12/2015 ........... A62B 23/025 |

* cited by examiner

CUSTOMIZED SEALING MEMBER FROM BLANK

CROSS-REFERENCE TO RELATED APPLICATIONS

This patent application claims the priority benefit under 35 U.S.C. § 371 of international patent application no. PCT/IB2016/057521, filed Dec. 12, 2016, which claims the priority benefit under 35 U.S.C. § 119(e) of U.S. Provisional Application No. 62/270,820, filed on Dec. 22, 2015, the contents of which are herein incorporated by reference.

BACKGROUND OF THE INVENTION

1. Field of the Invention

The present invention relates to non-invasive ventilation and pressure support systems wherein a patient interface device is used to deliver a flow of breathing gas to a patient, and in particular to customized sealing members and customized masks for patient interface devices. The present invention also relates to methods of manufacturing customized sealing members.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver positive airway pressure (PAP) therapy to treat certain medical disorders, the most notable of which is obstructive sleep apnea (OSA). Known PAP therapies include continuous positive airway pressure (CPAP), wherein a constant positive pressure is provided to the airway of the patient in order to splint open the patient's airway, and variable airway pressure, wherein the pressure provided to the airway of the patient is varied with the patient's respiratory cycle. Such therapies are typically provided to the patient at night while the patient is sleeping. Non-invasive ventilation and pressure support therapies as just described involve a gas flow generator to produce a flow of breathing gas, and the placement of a patient interface device including a mask component on the face of a patient. The gas flow generator produces positive air pressure by taking air in from the surroundings and spinning a fan to push the air out of the machine, through a delivery conduit, and into the patient interface device to be delivered to the patient.

Traditional masks include a sealing feature and a support feature that is connected to the sealing feature. The support feature compresses the face to create a robust seal and to mechanically couple the mask to the face to prevent the mask from moving throughout the night. The support feature, unlike the sealing feature, imparts relatively large compressive forces onto the face of the patient. The sealing feature is typically very thin and has minimal intrinsic strength. With current processes, in order to manufacture a fully customized sealing feature, a separate tool would have to be made, an approach that would not be cost effective or time efficient.

SUMMARY OF THE INVENTION

Accordingly, it is an object of the present invention to provide a customized sealing member and a customized mask including the customized sealing member. The steps to manufacture the customized sealing member include generating surface geometry data of a face of a patient, the surface geometry data corresponding to and representing a surface geometry of the face of the patient; generating customization data using the surface geometry data, the customization data representing how a seal blank should be modified for the patient; and customizing the seal blank using the customization data such that the customized seal blank is shaped according to the customization data.

The customized mask includes the customized sealing member; a support member; and a coupling member structured to couple the customized sealing member to the support member.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

As used herein, the singular form of "a," "an," and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs.

As used herein, the term "geometry" shall mean a three-dimensional profile of a surface or object. As used herein, the term "unitary" shall mean a homogeneous material having constant material properties throughout. As used herein, the term "geometry" shall mean a three-dimensional profile of a surface or object.

As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

As employed herein, the term "three-dimensional scanner" shall mean a device that analyzes a real-world object and generates data (e.g., digital data) that represents the shape of the object in three dimensions, and shall include, without limitation, contact scanners that probe the subject through physical touch to generate the shape data, non-contact active scanners that emit some kind of radiation or light and detect its reflection or passing through the object to generate the shape data, and non-contact passive scanners that detect reflected ambient radiation to generate the shape data.

As employed herein, the term "rendering" shall mean an image generated from two-dimensional or three-dimensional data that represents the shape of the object.

Figure 1:
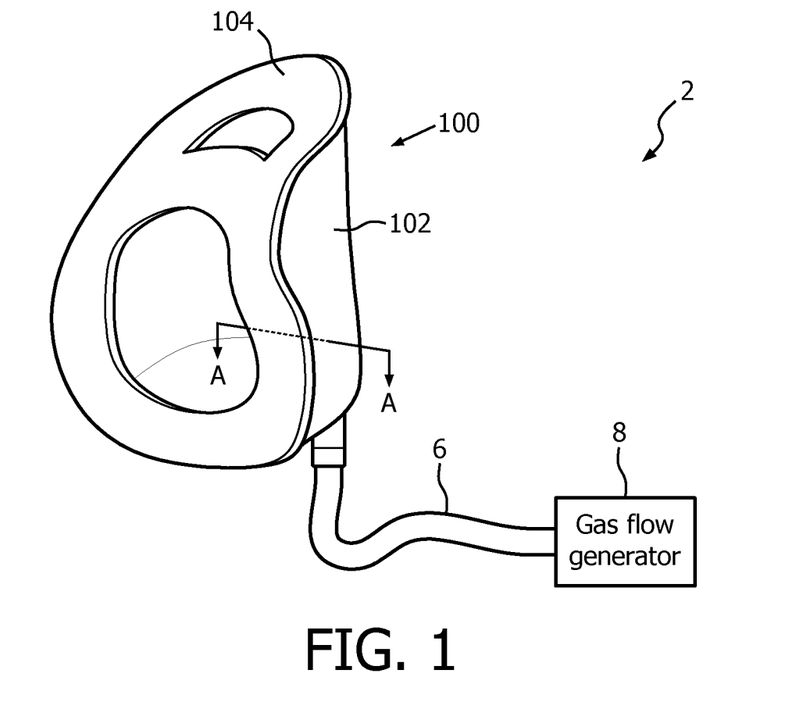
FIG. 1 is a simplified view of a pressure support system including a customized mask, in accordance with a non-limiting embodiment of the disclosed concept.
Figure 2:
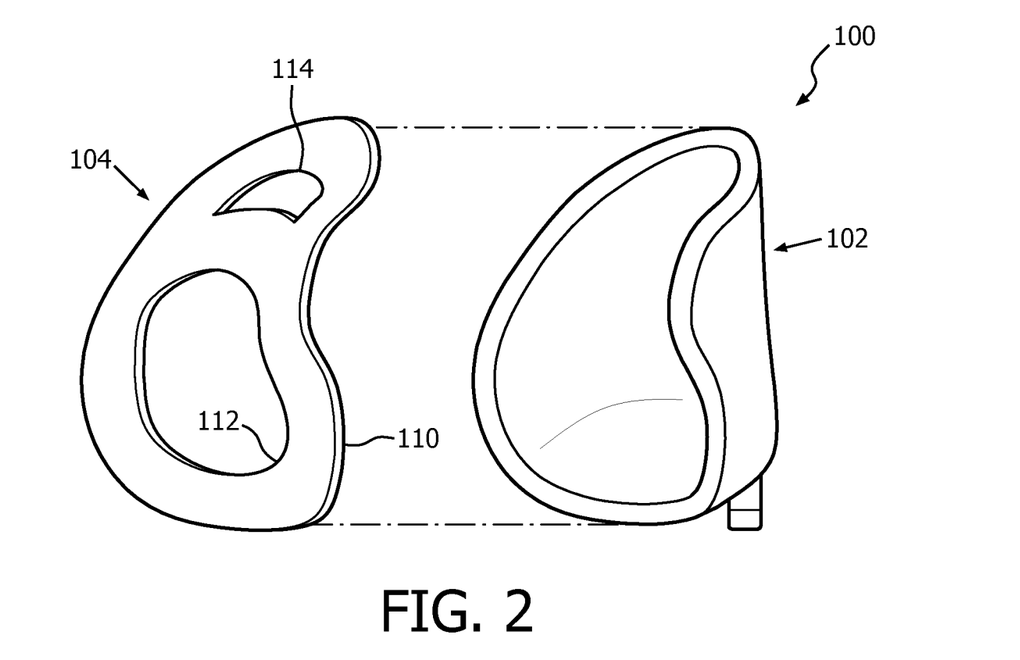
FIG. 2 is an exploded view of the customized mask for the pressure support system of FIG. 1.

FIG. 1 shows a pressure support system 2 that is structured to deliver pressure support therapy to a patient, in accordance with a non-limiting embodiment of the disclosed concept. As shown, pressure support system 2 includes a gas delivery conduit (e.g., hose 6, shown in simplified form), a gas flow generator 8 (shown in simplified form), and a customized mask 100. Hose 6 is structured to fluidly couple gas flow generator 8 to customized mask 100. FIG. 2 shows an exploded view of customized mask 100, which includes a support member 102 and a sealing member 104 structured to be coupled to support member 102. As will be discussed in greater detail hereinbelow, sealing member 104 is customized for the patient, advantageously providing a comfortable and reliable seal with the patient. This is distinct from prior art sealing members (not shown), which typically have the same geometry for all patients (e.g., not customized) and thus provide a seal with patients that is inferior to the seal created with sealing member 104.

Figure 3:
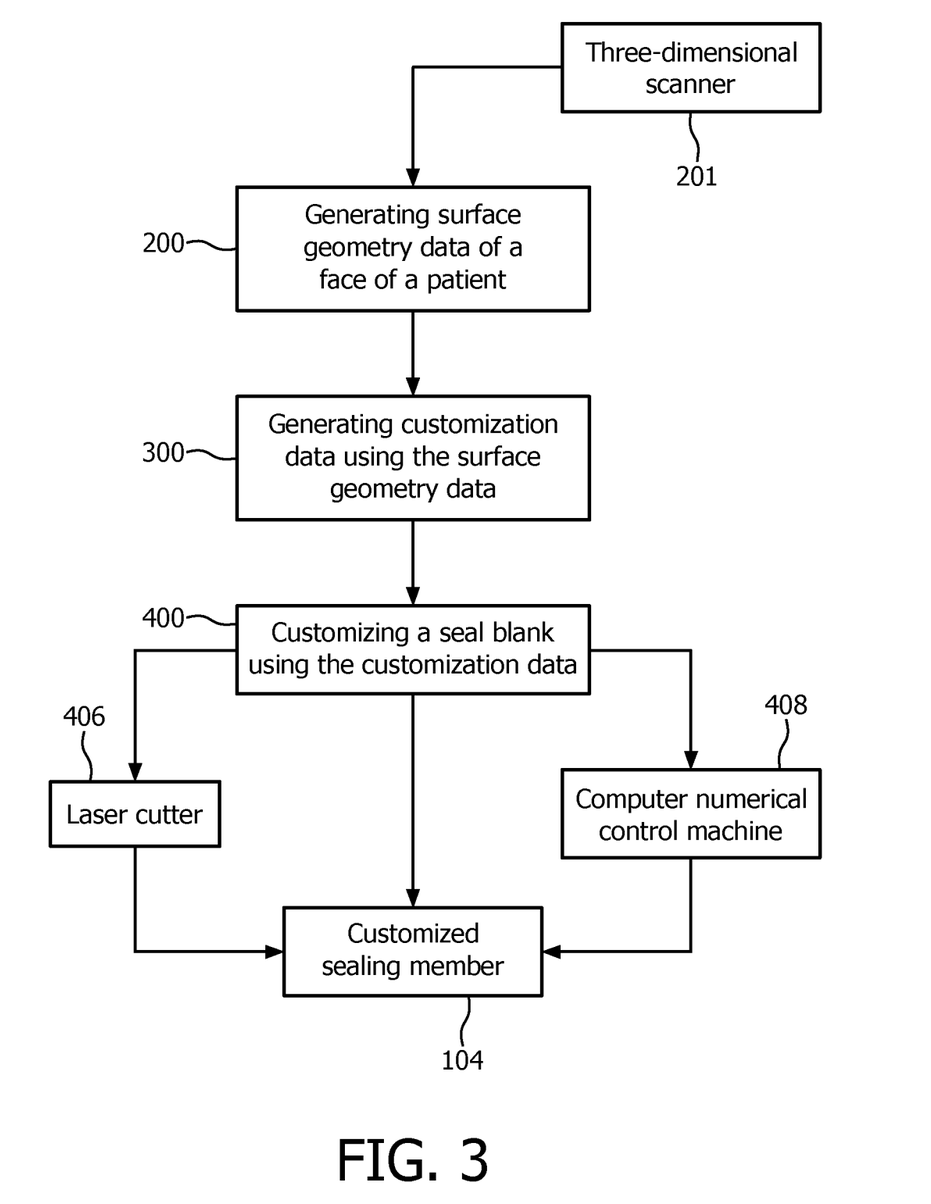
FIG. 3 is a schematic flow diagram, in block form, of a manufacturing process for a sealing member of the customized mask of FIG. 1.
Figure 4:
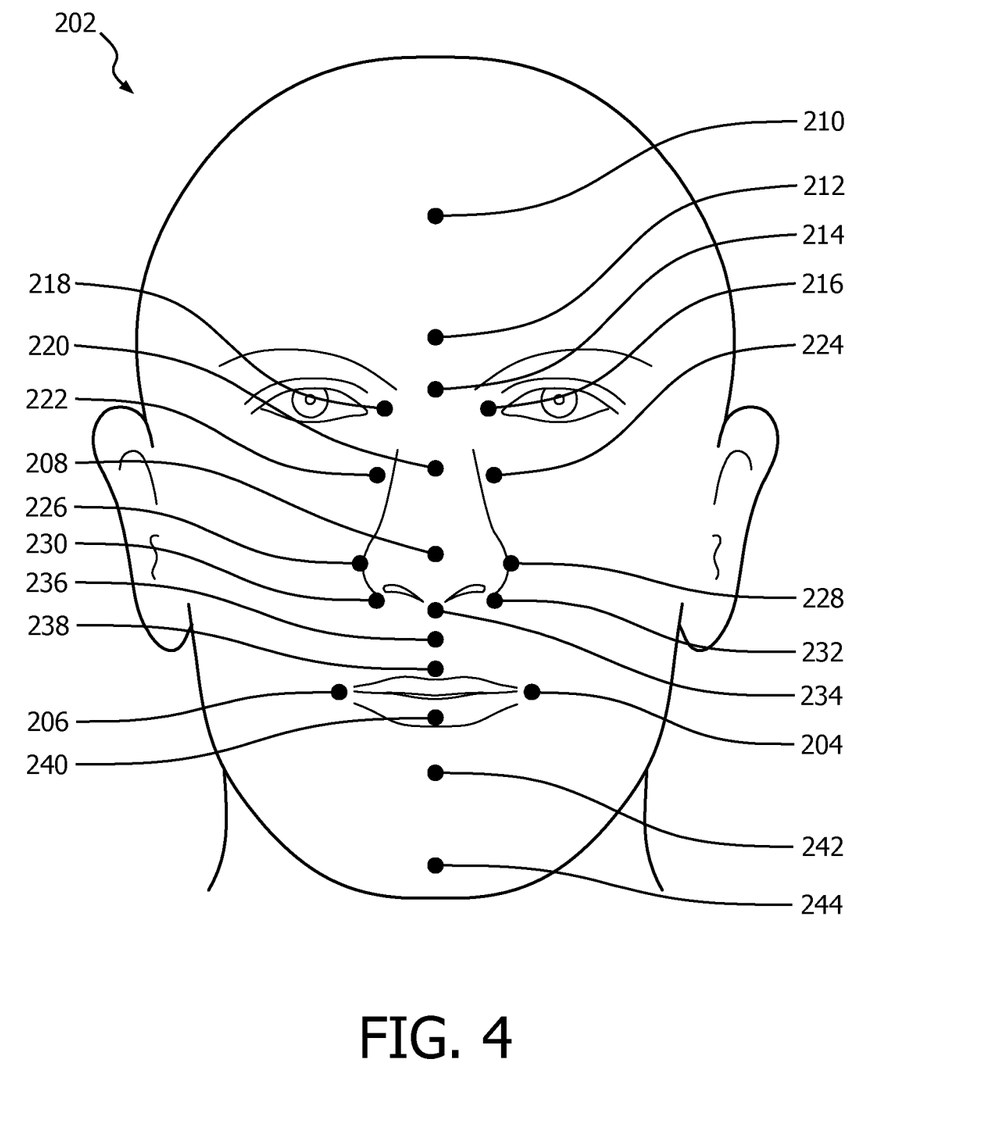
FIG. 4 is a top plan view of a rendering corresponding to surface geometry data of a face of a patient.

FIG. 3 shows a schematic diagram, in block form, of a process to manufacture customized sealing member 104. The first step 200 is generating surface geometry data that corresponds to and represents a surface geometry of the face of a patient. In one exemplary embodiment, the generating step 200 includes scanning the face of the patient with a three-dimensional scanner 201 to generate the surface geometry data. It will be appreciated that other suitable alternative methods of generating surface geometry data may also be employed without departing from the scope of the disclosed concept. An example rendering 202 corresponding to the surface geometry data generated in step 200 as shown on, for example, a computer screen, is shown in FIG. 4.

The next step 300 is generating customization data using the surface geometry data generated in step 200. The customization data represents how a seal blank (see, for example, seal blank 402, shown in FIG. 5) should be modified to form a customized seal for a particular patient. In the non-limiting exemplary embodiment, the customization data has data representing a set of three-dimensional coordinates that show where seal blank 402 is to be cut. For purposes of illustration, the three-dimensional coordinates are shown in FIG. 5 in dashed line drawing in the form of a number of curvilinear indicia (e.g., without limitation, edge portions 310, 312, 314).

Figure 5:
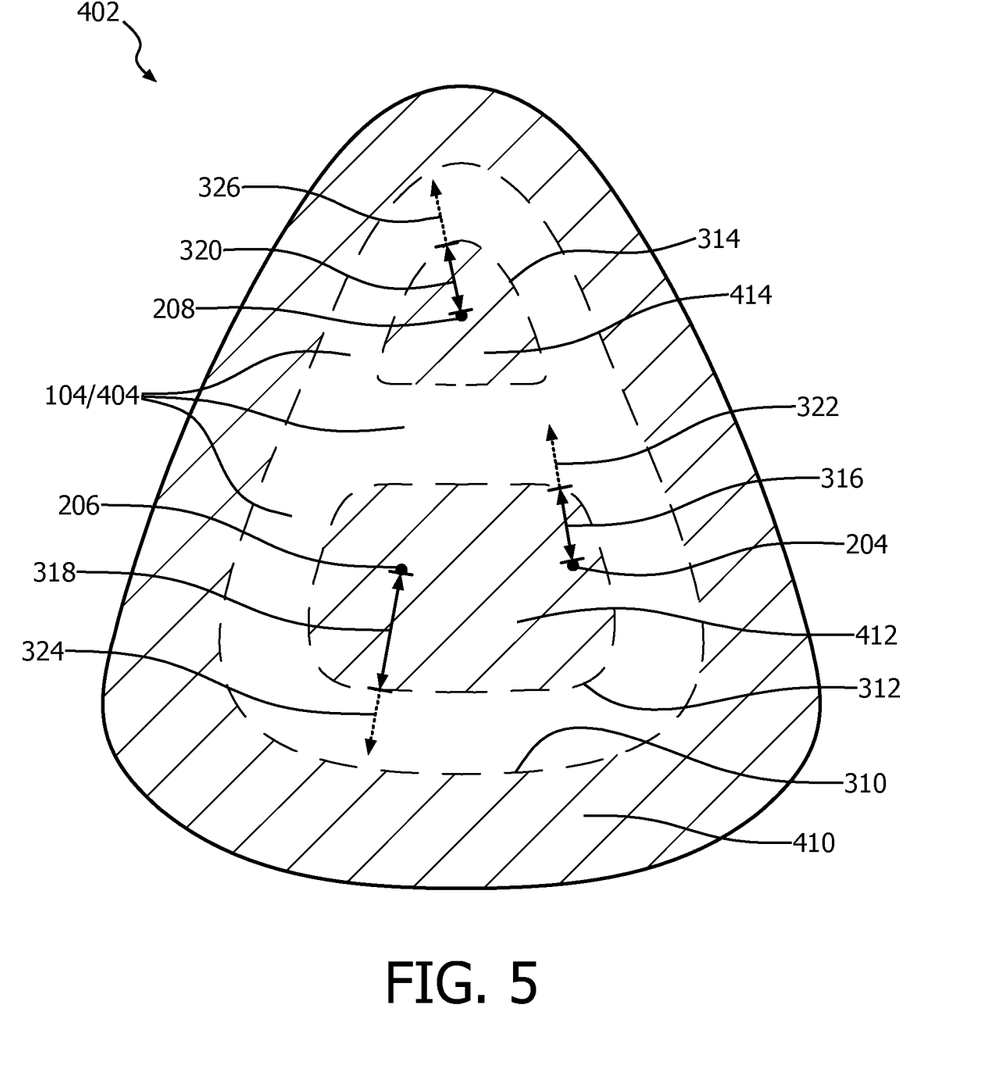
FIG. 5 is a top plan view of a seal blank employed in the manufacturing process of FIG. 3.

The manufacturing process further includes the step 400 of customizing seal blank 402 (FIG. 5) using the customization data to form the customized sealing member 104 shown in FIG. 2 (customized sealing member 104 is represented by portion 404 of seal blank 402, shown in FIG. 5, that remains after the customization of seal blank 402 is complete). As will be appreciated, customized sealing member 104 is shaped according to the customization data. In the exemplary embodiment, seal blank 402 has a predetermined contour shaped according to the surface geometry of the face of an average patient. That is, although FIG. 5 depicts a top view, seal blank 402 has a contour shaped to receive, for example, a nose, advantageously minimizing the force that would be exerted on the nose of the patient due to tension. Furthermore, any number of different seal blanks (not shown) may be employed for a given mask type and/or for different mask types. More specifically, within a given mask type (e.g., full-face mask type), different seal blanks may have different contours, such as, for example, a wider nose portion and/or longer cheek portions. Additionally, there may also be seal blanks for different mask types, such as, for example, nasal seal blanks, cradle style seal blanks, and pillows style seal blanks, in order to manufacture different respective customized masks.

As shown in FIG. 5 and as described herein, portion 404 represents customized sealing member 104. Accordingly, the customization data generated in step 300 is data (e.g., without limitation, cutting data indicating how cuts are to be made) that indicates a number of portions (see hatched portions 410, 412, 414 in FIG. 5, which are bounded by solid and dashed lines) of seal blank 402 that are to be removed to produce customized sealing member 104. Stated differently, before the customizing step 400, seal blank 402 is a relatively smooth component that is generally devoid of thru holes (i.e., has two opposing surfaces each being without internal edges), and during the customizing step 400, portions 410, 412, 414 are removed as indicated by the customization data. When removing portions 410, 412, 414, the customizing step 400 includes employing an apparatus (e.g., without limitation, a laser cutter 406, a computer numerical control machine 408) to cut seal blank 402 and thereby create customized sealing member 104. More specifically, in the exemplary embodiment, the customization data is sent to laser cutter 406 or to computer numerical control machine 408 in order to allow laser cutter 406 or computer numerical control machine 408 to cut seal blank 402 to produce customized sealing member 104.

Referring again to FIG. 4, one particular exemplary embodiment will now be described. As seen in FIG. 4, rendering 202 has a number of localized regions (e.g., without limitation, mouth corner regions 204, 206, nose tip region 208, central forehead region 210, bottom forehead region 212, nose bridge region 214, inner eye regions 216, 218, central nose bone region 220, central nose-cheek interface regions 222, 224, distal nose wing regions 226, 228, distal nose base regions 230, 232, central nose bottom region 234, central nasal landing region 236, central upper lip region 238, central lower lip region 240, central chin deep region 242, and chin apex region 244, each corresponding to a region of the face of the patient). In this exemplary embodiment, during the generating surface geometry data step 200, data corresponding to significant facial features of the patient (e.g., data corresponding to regions 204, 206, 208, 210, 212, 214, 216, 218, 220, 222, 224, 226, 228, 230, 232, 234, 236, 238, 240, 242, 244 is generated and that significant facial feature data is used to generate the customization data in step 300. Referring again to FIG. 5, regions 204, 206, 208 are shown superimposed onto seal blank 402.

In particular, in accordance with this exemplary embodiment of the disclosed concept, the generating customization data step 300 further includes employing a predetermined algorithm with the surface geometry data and the significant facial feature data to generate customization data that includes data representing edge portions 310, 312, 314 (in the form of three-dimensional coordinates). As can be seen in FIG. 5, the data representing edge portions 310, 312, 314 also delineates portions 410, 412, 414 that are to be removed to produce customized sealing member 104. In one particular exemplary embodiment, the predetermined algorithm generates the data representing edge portions 310, 312, 314 such that edge portions 310, 312, 314 are each spaced predetermined distances (see example distances 316, 318, 320 in FIG. 5) in predetermined directions (see example directions 322, 324, 326 in FIG. 5) from respective regions 204, 206, 208. For ease of illustration and economy of disclosure, only regions 204, 206, 208 are shown in FIG. 5, although it will be appreciated that regions 210, 212, 214, 216, 218, 220, 222, 224, 226, 228, 230, 232, 234, 236, 238, 240, 242, 244 (FIG. 4) may also be employed with the algorithm to generate the data representing edge portions 310, 312, 314. Although predetermined distances 316, 318, 320 and predetermined directions 322, 324, 326 have been disclosed herein in association with specific locations on edge portions 310, 312, 314, data representing the entirety of edge portions 310, 312, 314 is generated by way of the algorithm calculating an infinite number of predetermined distances in an infinite number of predetermined directions from regions 204, 206, 208.

In this exemplary embodiment, edge portions 310, 312, 314 represent, for example, cut lines where seal blank 402 is to be cut. Accordingly, during the customizing step 400, the customization data including the data representing edge portions 310, 312, 314 is used by one of apparatuses 406, 408 to customize seal blank 402 by removing portions 410, 412, 414. Apparatuses 406, 408 each include an alignment feature that allow the respective apparatuses 406, 408 to locate seal blank 402 before seal blank 402 is cut. During the customizing step 400, the customization data including the data representing edge portions 310, 312, 314 is sent to one of apparatuses 406, 408, which performs the cutting operation based on the received data and the alignment feature.

It follows that because the data representing edge portions 310, 312, 314 is generated using the surface geometry data particular to the patient (i.e., spacing edge portions 310, 312, 314 predetermined distances 316, 318, 320 in predetermined directions 322, 324, 326 from localized regions 204, 206, 208), resulting sealing member 104 is customized and shaped according to the face of the patient. As a result, when customized sealing member 104 is employed in customized mask 100, the seal between the patient and customized mask 100 is more comfortable and reliable, as compared to a seal between a mask (not shown) including a non-customized sealing member and the patient. For example, the spacing between the actual mouth corners and nose tip of the patient and a number of edge portions 110,112,114 (FIG. 2) of sealing member 104 will be unique to the patient. This results from the algorithm spacing edge portions 310, 312, 314 predetermined distances 316, 318, 320 from regions 204, 206, 208. Furthermore, the disclosed method may be employed to generate customization data for any number of different patients. That is, surface geometry data corresponding to different faces will have different localized regions. Customization data can then be generated based on the respective localized regions and the predetermined algorithm, and seal blank 402 and/or a suitable alternative seal blank (not shown) may be customized using the customization data.

Although the disclosed concept has been described in association with an exemplary embodiment wherein the customization data is in the form of data representing a number of specific portions of seal blank 402 that are to be removed, it is also within the scope of the disclosed concept for the customization data to instead represent the entire finished geometry of the desired customized sealing member 104. In such an implementation, that customization data would be sent to an apparatus such as laser cutter 406 or computer numerical control machine 408 which in turn would use that data to determine how the seal blank should be modified to produce the desired customized sealing member 104 (i.e., the apparatus would use the received customization data representing the entire finished geometry to determine what portions of the seal blank 402 would need to be removed, and then remove the portions accordingly). In other words, the customization data may, in an alternative embodiment, represent the geometry of customized sealing member 104.

Figure 6:
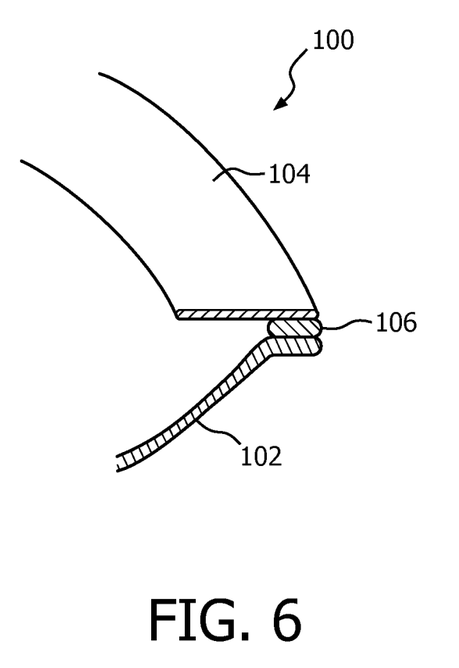
FIG. 6 is a cross-sectional view of the customized mask of FIG. 1, taken along line A-A of FIG. 1.

FIG. 6 shows a section view of customized mask 100 according to another exemplary embodiment. As shown, customized mask 100 in this embodiment further includes a coupling member (e.g., adhesive bead 106) structured to adhesively bond support member 102 to customized sealing member 104. Adhesive bead 106 extends along the entire periphery of customized mask 100 in order that support member 102 and sealing member 104 are properly coupled. Support member 102 may also be coupled to sealing member 104 by any suitable alternative known method (e.g., adhesive tape). Additionally, in the exemplary embodiment, support member 102 is customized and is made of a relatively rigid and unitary material (i.e., a material having a constant modulus of elasticity between 400 and 3,000 megapascals). However, it is within the scope of the disclosed concept for customized sealing member 104 to be employed with any suitable alternative support member (not shown), without departing from the scope of the disclosed concept. That is, customized sealing member 104 may be employed in a mask with a support member (not shown) that is customized and made of relatively soft materials (e.g., materials softer than the material of support member 102), or, that is non-customized and made of relatively soft materials.

Figure 7:
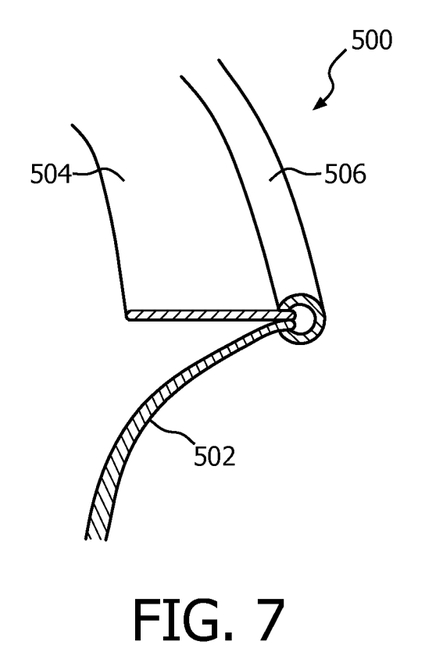
FIG. 7 is a cross-sectional view of a customized mask, in accordance with another non-limiting embodiment of the disclosed concept.
Figure 8:
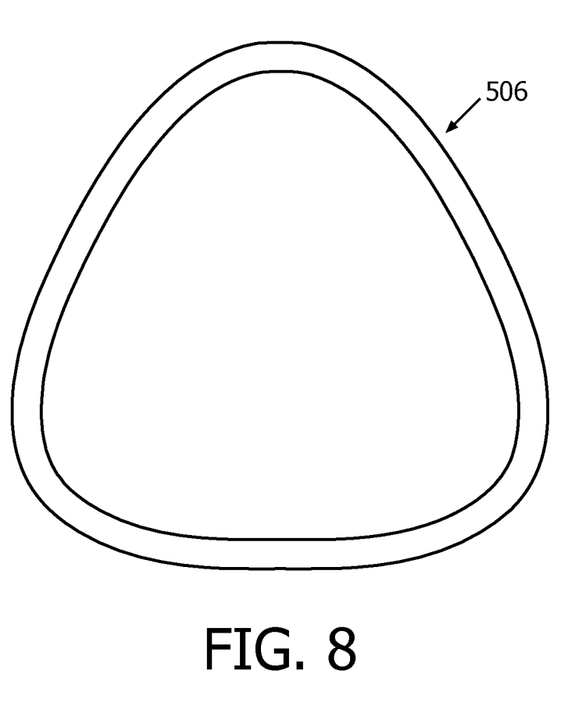
FIG. 8 is a top plan view of a coupling member for the customized mask of FIG. 7.

FIG. 7 shows a section view of another customized mask 500 according to a further exemplary embodiment, which includes a support member 502, a customized sealing member 504, and a relatively rigid coupling member 506 structured to couple support member 502 to sealing member 504 by a snap-action mechanism. Customized sealing member 504 is made by the same process as customized sealing member 104, described hereinabove. As shown, coupling member 506 generally has a C-shaped cross-section. FIG. 8 shows a top plan view of coupling member 506. It will be appreciated that coupling member 506, which is also generally annular-shaped, is structured to extend along the entire periphery of customized mask 500 in order to properly couple support member 502 to sealing member 504. In the exemplary embodiment, coupling member 506 is made of a unitary material that has a modulus of elasticity between 400 and 3,000 megapascals. That is, if a given location of coupling member 506 has a modulus of elasticity of 1,000 megapascals (e.g., or any other modulus of elasticity of between 400 and 3,000 megapascals), every other location of coupling member 506 has the same modulus of elasticity (i.e., in the case of 1,000 megapascals, every other location of coupling member 506 has a modulus of elasticity of 1,000 megapascals).

Coupling member 506 is shaped differently than (i.e., does not coincide with) the surface geometry of the patient, advantageously allowing for a comfortable engagement, despite the rigidity of the material of coupling member 506. More specifically, coupling member 506 is structured to compress (i.e., displace) the cheek regions of the face of the patient more than the relatively stiff nose bridge region and chin region such that the contact pressure (i.e., force per unit area) is in a relatively comfortable range for all regions of the face of the patient. This is distinct from typical prior art mask constructions, in which the geometry of the mask is structured to correspond exactly to the geometry of the face of the patient, a construction that would result in undesirable discomfort and/or pain to a patient if a coupling member were to be made of rigid materials having moduli of elasticity similar to that of coupling member 506.

Although the disclosed concept has been described in association with sealing members 104, 504 and coupling members 504, 506 in customized masks 100, 500, it will be appreciated that other suitable alternative sealing members and/or coupling members made by processes similar to those used to manufacture sealing members 104, 504 and coupling member 506, respectively, may be employed in other customized masks (e.g., without limitation, customized nasal masks, customized cradle style masks, customized pillows style masks) without departing from the scope of the disclosed concept.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A method of manufacturing, from a seal blank, a customized sealing member for a customized mask of a pressure support system, the method comprising the steps of:
   generating surface geometry data of a face of a patient, the surface geometry data corresponding to and representing a surface geometry of the face of the patient, the surface geometry data having first data representing one or more localized regions corresponding to facial features of the patient;
   generating customization data using the surface geometry data, the customization data representing one or more edge portions defining one or more regions to be removed from the seal blank to create one or more thru holes in the seal blank, wherein generating the customization data includes spacing the one or more edge portions from corresponding one or more of the localized regions based on predetermined directions and distances from the one or more localized regions; and
   customizing the seal blank using the customization data such that the one or more regions to be removed from the seal blank are removed to create one or more thru holes in the seal blank to produce the customized sealing member, wherein the customized sealing member includes the one or more thru holes and does not include the one or more regions removed from the seal blank.

2. The method according to claim 1, wherein the one or more localized regions are selected from the group consisting of a mouth corner region, a nose tip region, a central forehead region, a bottom forehead region, a nose bridge region, an inner eye region, a central nose bone region, a central nose-cheek interface region, a distal nose wing region, a distal nose base region, a central nose bottom region, a central nasal landing region, a central upper lip region, a central lower lip region, a central chin deep region, and a chin apex region.

3. The method according to claim 1, customizing the seal blank further comprises:
   cutting the seal blank with an apparatus selected from the group consisting of a computer numerical control machine and a laser cutter using the customization data.

4. The method according to claim 1, wherein generating surface geometry data further comprises:
   scanning the face of the patient with a three-dimensional scanner to generate the surface geometry data.

5. The method according to claim 1, wherein the seal blank is a smooth component devoid of thru holes.

* * * * *